United States Patent [19]
Casey et al.

[11] Patent Number: 5,914,247
[45] Date of Patent: Jun. 22, 1999

[54] METHOD AND SYSTEM FOR DETECTING FECAL AND INGESTA CONTAMINATION ON THE CARCASSES OF MEAT ANIMALS

[75] Inventors: Thomas A. Casey, Ames; Mark A. Rasmussen, McCallsburg; Jacob W. Petrich, Ames, all of Iowa

[73] Assignees: The United States of America as represented by the Secretary of Agriculture, Washington, D.C.; Iowa State University Research, Ames, Iowa

[21] Appl. No.: 09/033,754

[22] Filed: Mar. 3, 1998

[51] Int. Cl.⁶ .............................. C12Q 1/04; C12Q 1/00; G01N 33/53
[52] U.S. Cl. .................... 435/34; 435/968; 435/4
[58] Field of Search .................... 435/34, 968, 4

[56] References Cited

U.S. PATENT DOCUMENTS

| | | | |
|---|---|---|---|
| 4,631,413 | 12/1986 | Jensen et al. | 250/458.1 |
| 4,866,283 | 9/1989 | Hill | 250/461.2 |
| 4,939,574 | 7/1990 | Petersen et al. | 435/34 |
| 5,474,910 | 12/1995 | Alfano | 435/34 |
| 5,621,215 | 4/1997 | Waldroup et al. | 435/341 |
| 5,658,798 | 8/1997 | Bertin et al. | 436/3 |

OTHER PUBLICATIONS

Schreiber, U., Detection of rapid induction kinetics with a new type of high–frequency modulated chlorophyll fluorometer, *Photosynthesis Research* 9, 1986, pp. 261–272.

Anderson, D.M. et al., The potential of laster–induced fluorescense (LIF) spectra of sheep feces to determine diet botanical composition, *Small Ruminant Research*, 21, 1996, pp. 1–10.

Wagner, John S., et al., Rapid Optical Detection of Transmissible Spongiform Encphalopathies (TSE), Food Pathogens and Other Biological and Non–Biological Material, General Solicitation Letter, 1997.

Schreiber, U., Chlorophyll Fluorescence as a Nonintrusive Indicator for Rapid Assessment of In Vivo Photosynthesis, Schulze E–D and Caldwell MM (eds) Ecophysiology of Photosynthesis, 1994, vol. 100, pp. 49–70, Springer, Berlin.

*Primary Examiner*—Louise N. Leary
*Attorney, Agent, or Firm*—M. Howard Silverstein; Randall E. Deck; John D. Fado

[57] ABSTRACT

A method and apparatus for detecting ingesta or fecal contamination on an animal carcass using fluorescent spectroscopy is disclosed. The surface of the carcass is illuminated with UV or visible light having an appropriate wavelength and fluorescent light emissions having a wavelength between about 660 to 680 nm are then detected. The emission of fluorescent light having wavelengths between about 660 to 680 nm is an indication of the presence of ingesta or fecal material on the carcass.

20 Claims, 5 Drawing Sheets

METHOD AND SYSTEM FOR DETECTING FECAL AND INGESTA CONTAMINATION ON THE CARCASSES OF MEAT ANIMALS

BACKGROUND OF THE INVENTION

1. Field of the Invention

The invention relates to an improved method and apparatus for detecting fecal or ingesta contamination on the carcasses of animals during and after slaughter using visible light fluorescent spectroscopy.

2. Description of the Prior Art

Microbial pathogens in food cause an estimated 6.5 million to 33 million cases of human illness and up to 9,000 deaths annually, according to the Council for Agricultural Science and Technology. Furthermore, the USDA Economic Research Service has recently reported that the annual cost of the food-borne illnesses caused by six common bacterial pathogens, Campylobacter spp., *Clostridium perfringens, Escherichia coli* 0157:H7, *Listeria monocytogenes,* Salmonella spp., and *Staphylococcus aureus,* ranges from 2.9 billion to 6.7 billion dollars (Food Institute Report, USDA, AER, December, 1996). The foods most likely to cause these illnesses are animal products such as red meat, poultry and eggs, seafood, and dairy products.

Contamination of meat and poultry in particular with many bacterial food-borne pathogens often occurs as a result of exposure of the animal carcass to ingesta and/or fecal material during or after slaughter. Any of the above-mentioned pathogens can be transmitted to humans by consumption of meat and poultry contaminated in this manner. However, the contamination of carcasses with feces or ingesta is the primary source of contamination of meat and poultry with particularly onerous pathogens, including Campylobacter spp., *Escherichia coli* 0157:H7, and Salmonella spp.

After slaughter, each carcass is examined for disease or evidence of contamination that would render all or part of the carcass unfit for human consumption. Currently, the meat packing industry relies upon a variety of methods for the inspection of animal carcasses. These methods typically include human visual inspection, microbiological culture analysis, bioluminescent ATP-based assays, and antibody-based microbiological tests. Unfortunately, these procedures are labor intensive, time consuming, and insensitive, and do not meet the needs of the packing industry for an accurate, high speed, non-destructive method that is amenable to inspection and real-time analysis.

Fluorescence spectroscopy has been commonly used for the analysis of a variety of compounds, microorganisms, and tissues. The use of fluorescence spectroscopy for the detection of contaminants on foods has also been previously disclosed. For example, Alfano (U.S. Pat. No. 5,474,910) disclosed a method and apparatus for detecting biological molecules and microorganisms by irradiating the sample material with UV light at a wavelength between about 250 to 325 nm and measuring the resultant fluorescence. Alfano further disclosed that the process could be used for detecting the bacterial spoilage of food products, including meat and poultry. More recently, Waldroup and Kirby (U.S. Pat. No. 5,621,215) disclosed a method and apparatus for detecting the contamination of meat or poultry with ingesta or fecal material. As described therein, the meat or poultry is illuminated with UV light having a wavelength between about 320 to 420 nm, and examined for fluorescence, specifically UV fluorescence. Despite these advances, there exists a continuing need for a high-speed system for detecting ingesta or fecal contamination of carcasses with increased sensitivity and accuracy.

SUMMARY OF THE INVENTION

We have now invented a novel and improved method and apparatus for detecting ingesta or fecal contamination on the surface of a freshly slaughtered animal carcass using visible light fluorescent spectroscopy. In this process, the carcass is illuminated with UV or visible light having a wavelength effective to elicit fluorescence of feces at a wavelength between about 660 to 680 nm, which fluorescent light emissions having a wavelength between about 660 to 680 nm are then detected. The emission of fluorescent light having wavelengths between about 660 to 680 nm is an indication of the presence of ingesta or fecal material on the carcass. In its simplest form, the apparatus for practicing the invention includes an excitation source such as a lamp or laser for illuminating the surface with UV or visible light having a wavelength effective to elicit fluorescence of feces at a wavelength between about 660 to 680 nm, and a detector for collecting the fluorescent light emissions having a wavelength between about 660 to 680 nm.

In accordance with this discovery, it is an object of this invention to provide an improved method and apparatus for detecting the presence of ingesta or fecal contamination on the surface of meat or animal carcasses to improve the safety of the food supply.

Another object of the invention is to provide an improved high-speed method and apparatus which is capable of near real time detection of ingesta or fecal contamination on the surface of animal carcasses, which would not interfere with existing slaughterhouse line speeds or procedures.

Yet another object of the invention is to provide an improved method and apparatus for the detection of ingesta or fecal contamination on the surface of animal carcasses with increased sensitivity and accuracy and which is substantially free from non-specific background interference.

Other objects and advantages of the invention will become apparent from the ensuing description.

DETAILED DESCRIPTION OF THE INVENTION

Figure 1:
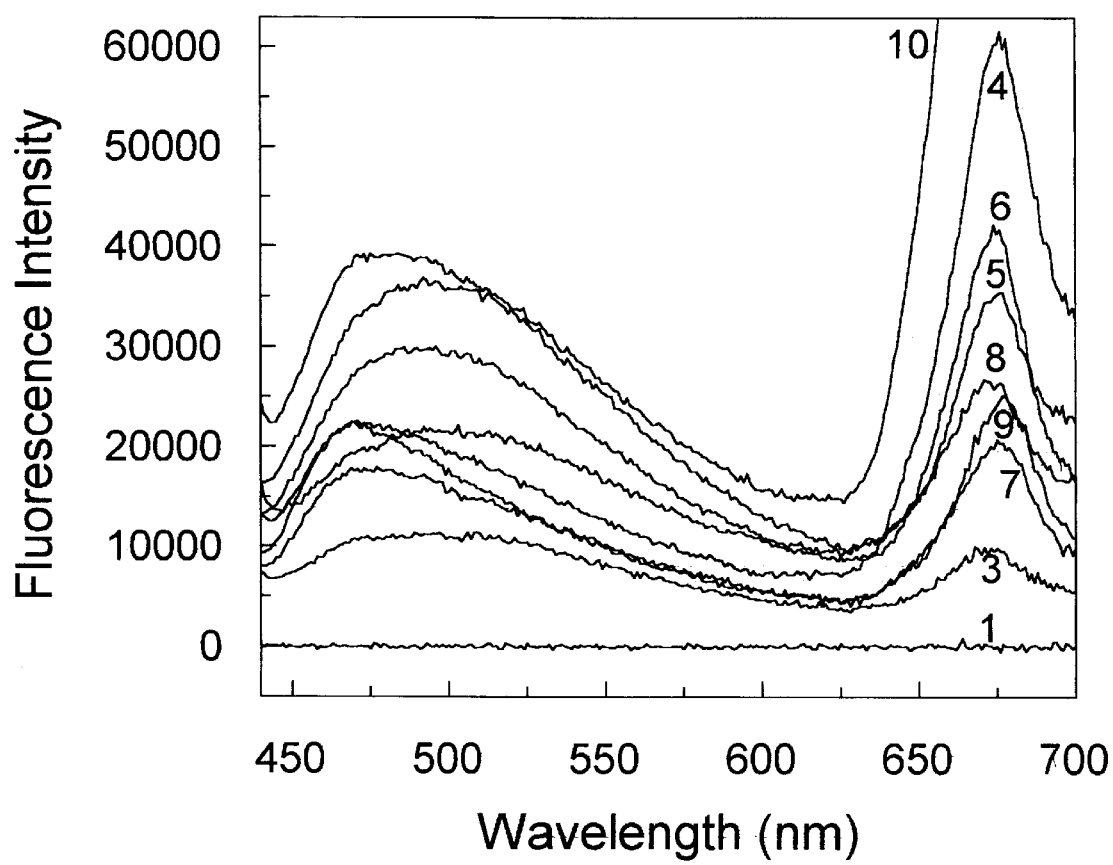
FIG. 1 is the emission spectra of ingesta and feces of different plant consuming animals excited with 430 nm light. Sample 1 is a buffer solution which serves as a negative control. Samples 3–10 are cow #1 rumen contents, cow #1 cecum contents, cow #1 feces, pig feces, cow #2 rumen contents (refrigerated), cow #2 feces (refrigerated), cow #2 rumen contents (fresh), and cow #2 feces (fresh), respectively.

The process and apparatus of this invention may be used for detecting the ingesta or feces from any plant eating animal on the surface of animal carcasses, particularly during or shortly after slaughter and evisceration. The invention is particularly applicable to the detection of ingesta or feces on the carcass of wild or domestic meat producing animals, including but not limited to facultatively herbivorous or plant eating mammals and birds such as bovine, poultry, porcine, ovine, caprine, equine, and ratites, especially cattle and calves, hogs, chickens, turkeys, sheep, and goats.

Generally, testing of the carcasses is conducted at one or more stations along the slaughterhouse line, during transport along the line, or soon after completion of slaughter. As the carcasses pass the testing stations, they may be illuminated and any fluorescent light emitted therefrom detected as described hereinbelow. Because slaughterhouse practices vary with the particular meat producing animal, specific locations for testing along the slaughterhouse line will vary. For instance, the typical slaughter of beef cattle includes the following steps: the animal is rendered unconscious, shackled and hoisted onto a moving rail or line, exsanguinated, skinned (manually or in combination with mechanical hide pullers), and decapitated. The ends of the digestive tract may be tied off (to prevent contamination) prior to evisceration which is conducted using a deep, midline abdominal incision. The entrails are then removed onto a conveyor for inspection and further processing or disposal. The eviscerated carcass may then be split into halves by cutting longitudinally through the spinal column. These halves are inspected for quality and for nonedible defects (e.g. tumors). Those that pass inspection are then weighed and hung in a chiller room for approximately 24 hours before further processing or shipment. Swine slaughterhouse procedures are similar to beef cattle except some swine are not skinned but instead are washed and flamed to remove body hair, and swine intended for use in sausage may not be chilled but may be deboned while warm, ground with other ingredients such as spices, and quickly chilled to preservation temperatures. Poultry slaughterhouse procedures on the other hand differ significantly, and include the following steps: the bird is hung by the legs, electrically stunned, decapitated, scalded and defeathered, gutted (usually by mechanical means), and soaked in chlorinated water chilling baths. Testing may be conducted during or upon completion of any of the abovementioned steps, or within approximately 1 hour of completion of slaughter (within about 1 to 2 hours of initiation of slaughter).

In a particularly preferred embodiment, ruminant (e.g. bovine), and swine carcasses will be tested for contamination prior to chilling of the split carcasses, usually within about 1 hour after splitting or about 1 to 2 hours after initiation of slaughter. Other preferred sites for testing include prior to, during or after skinning or evisceration/gutting. Poultry carcasses are preferably tested for contamination during or after defeathering or gutting. Poultry may also be tested following removal from chilling baths for quality control monitoring. All surfaces of the carcass should be examined, including internal and external surfaces thereof. The examination of internal surfaces is of particular importance for the detection of contamination within the body cavity of animals such as fowl which are mechanically gutted and may not be split.

Detection of ingesta and feces in accordance with this invention is based upon applicants' discovery that the ingesta and feces of plant eating animals exhibit fluorescence at wavelengths between about 660 to 680 nm when illuminated with appropriate UV or visible excitation light, such as light having wavelengths between about 300 to 600 nm, particularly between about 400 to 440 nm or 510 to 600 nm. This optical characteristic is ubiquitous in animals that are consuming plant material, particularly plant material containing photosynthetic pigments such as chlorophyll. The emission spectra of ingesta and feces from a variety of plant consuming animals excited at 430 nm are shown in FIG. 1.

In practice, the surface of the carcass to be examined for contamination is illuminated with UV or visible light having one or more wavelengths which are effective to elicit fluorescence of the feces of a plant consuming animal at a wavelength between about 660 to 680 nm. Without being limited thereto, suitable wavelengths of excitation light are between about 300 to 600 nm, preferably between about 400 to 440 nm or between about 510 to 600 nm, and most preferably between about 410–430 nm and/or between about 520–540 nm. The illuminated surface is then examined for the emission of fluorescent light having a wavelength between about 660 to 680 nm, preferably between about 670–675 nm. Detection of fluorescent light emissions between about 660 to 680 nm indicates the presence of ingesta or fecal material on the surface. Without wishing to be limited by theory, it is believed that light having any wavelength between about 300 to 600 nm is effective to excite plant pigments like chlorophyll and digestive metabolites of these pigments like the chlorophyll metabolite, pheophytin, present within the ingesta or excreta, and thereby cause these components to emit fluorescent light having a wavelength between about 660 to 680 nm.

The specific wavelength used for illumination may be readily determined by the user. Generally, light having a wavelength between 400 to 440 nm is intensely absorbed by the ingesta and feces of the plant consuming animals, and therefore elicits the highest intensity of fluorescence in the prescribed 660 to 680 range. In contrast, the absorption spectra of the ingesta and feces between 510 to 600 nm is significantly lower, and consequently the intensity of the fluorescence is less than that attained by illuminating with 400 to 440 nm light of the same intensity. However, despite this lower absorption, illumination with 510 to 600 nm light, particularly between 520–540 nm, may be preferable due to the ready availability and low cost of lasers producing light within this range.

Upon detection of ingesta or fecal contamination, the carcass may be washed, disinfected or otherwise treated to remove ingesta or feces from the surface thereof. The process for detecting ingesta and feces on the washed surface is then repeated, followed by additional washing and/or disinfection steps if necessary, until all traces of ingesta or feces have been removed or destroyed. A variety of wash solutions or disinfectants are known in the art and are suitable for use herein and include but are not limited to pressurized water or steam sprays, organic acids, chlorinated water, hypochlorous acid, detergents, and treatment with radiation. Once the carcass has been determined to be free of contamination as evidenced by the lack of fluorescence at the described range, the carcass may be subjected to further processing or shipped.

The detection of ingesta or fecal contamination on the carcass also allows the meat processor to adjust and improve upstream processing steps in order to prevent contamination wherever possible, increase sanitation, and improve meat quality.

In a preferred embodiment, to minimize the possibility of false positives from background fluorescence or stray light and to enhance contrast, the intensity of fluorescent light emissions measured at 660–680 nm are correlated to the intensity of fluorescent light emissions at the baseline or level of minimum intensity of the spectral curve of the carcass being examined. This correlation may also be used for a quantitative determination of feces or ingesta on the carcass. The baseline may be measured at several different wavelengths which may be determined by examination of the fluorescent spectrum of the subject carcass. However, we have discovered that the baseline value for any carcass may be consistently determined by measuring the intensity of fluorescent light emissions at about 610–620 nm, preferably at about 610 nm. Thus, following illumination with excitation light, the intensity of fluorescent light emissions are quantitatively measured at both a wavelength between about 660–680 nm and at a wavelength between about 610–620, and the measured values are then compared. For example, in its simplest form, the measured intensity at 610–620 nm may be electronically subtracted from the measured intensity at 660–680 nm, or the ratio of the intensities may be determined. The resultant corrected intensity exhibits greater contrast with the background than carcasses examined for fluorescence without this correlation.

In another preferred embodiment, testing incorporates phase sensitive or phase lock (lockin) techniques. Testing in this manner allows quantitative measurements to be made in real time and in ambient light conditions, without using a light-tight testing chamber. The skilled practitioner will recognize that other spectroscopic techniques such as boxcar or gated integration techniques may also be used. In accordance with phase sensitive techniques, the excitation light is modulated at a predetermined frequency, for example, by mechanically chopping the light beam with a spinning wheel. Or, the excitation source may be light emitting diodes controlled by high frequency pulse generators. This modulated excitation source will in turn yield fluorescence from a contaminated carcass that is modulated at the same frequency. The fluorescence signals emitted from the carcass are then selectively detected at the same frequency as the modulated excitation light; only emitted fluorescent light at the same frequency is detected and amplified. Hence, no fluorescence signals due to stray or ambient light are detected. A detailed description of phase sensitive spectroscopic techniques which are suitable for use herein may be found, for example, in Horowitz and Hill (The Art of Electronics, Cambridge University Press, Cambridge, pp. 628–631), Shoemaker et al. (Experiments in Physical Chemistry, 5th ed., McGraw-Hill, New York, p. 737), Zanowsky (1996, Laser Focus World, 32:135–137), Ingle and Crouch (Spectrochemical Analysis, Prentice-Hall, New York, 1988, especially at pp. 125, 410, and 526), Fleming (Chemical Applications of Ultrafast Spectroscopy (Oxford Press, New York, 1986, especially at chapter 3), and Schreiber (1986, Photosynthesis Research, 9:261–272), the contents of each of which are incorporated by reference herein.

Figure 2:
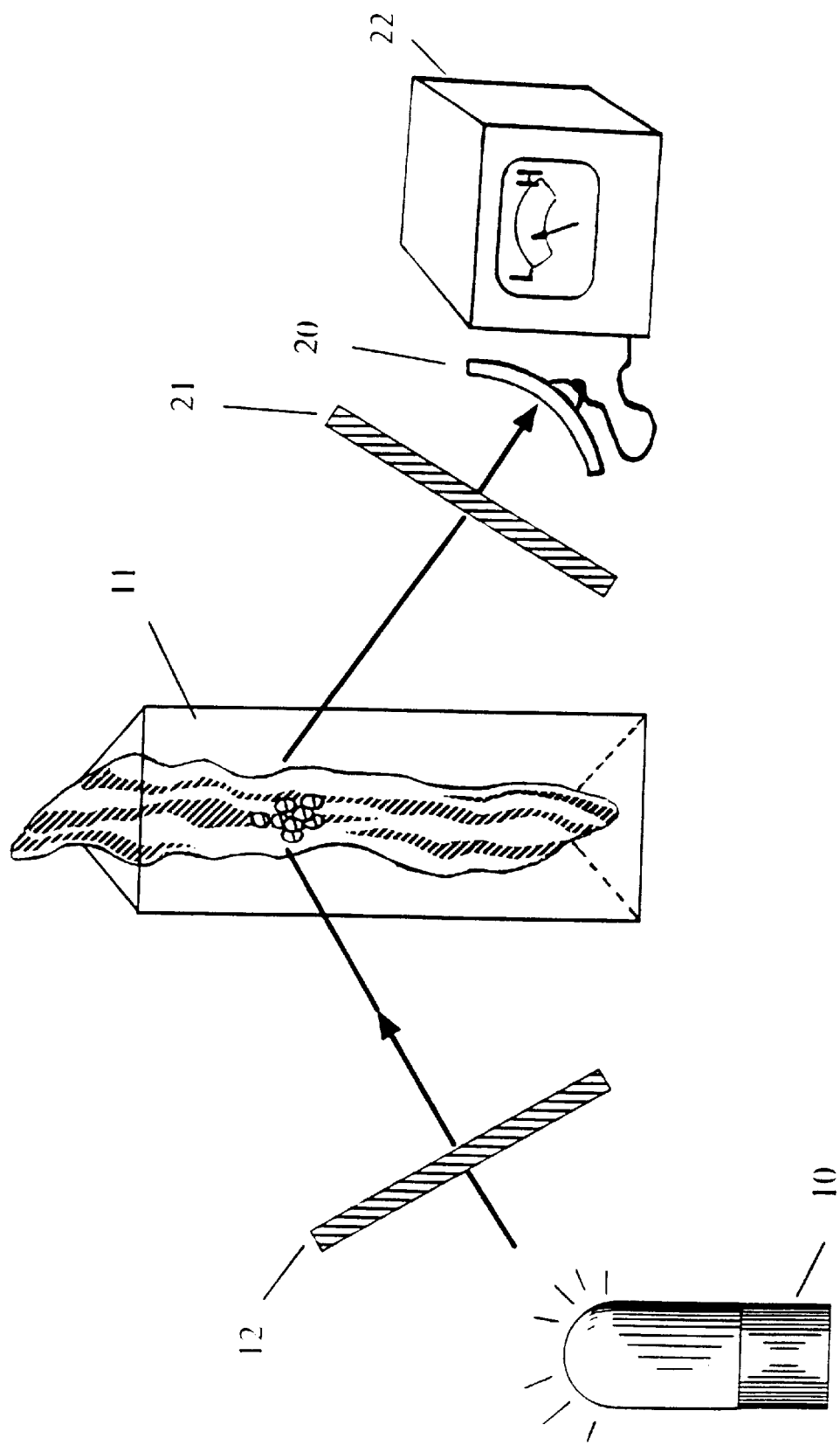
FIG. 2 is a schematic diagram of the disclosed process and apparatus.

As shown in FIG. 2, the apparatus of the invention includes an excitation light source 10 which illuminates the surface of the carcass 11. For use herein, the excitation light source should emit electromagnetic radiation which is effective to elicit or cause the fluorescence of the feces of a plant consuming animal at a wavelength between about 660 to 680 nm. Without being limited thereto, generally the excitation sources should emit UV or visible light having a wavelength in the range of about 300–600 nm, preferably between about 400–440 nm or between about 510–600 nm, and particularly between about 410–430 nm and/or 520–540 nm, to cause ingesta or fecal material on the carcass to produce fluorescent radiation. A variety of coherent or incoherent excitation light sources are suitable for use herein, and include but are not limited to lasers, light emitting diodes (LED's), and arc lamps, and the light source may be continuous or pulsed. However, lasers emitting at an appropriate excitation wavelength are generally preferred. An optional optical filter 12 is preferably provided which permits only light of the selected excitation wavelength to pass therethrough onto the carcass 11.

Fluorescent light emitted from the surface of the carcass 11 is detected using a photodetector 20 sensitive to at least 660–680 nm light. Without being limited thereto, suitable photodetectors 20 for use herein include photodiode detectors, photomultipliers, amplifiers or image intensifiers, CCD cameras, and photocathodes and microchannel plates (i.e. "Night vision" technology). One or more optical filters 21 are preferably positioned between the carcass and the photodetector to selectively transmit light in the range of about 660–680 nm light while preventing transmission of back-scattered excitation light. Filters 21 are preferably effective to remove wavelengths of light less than about 660 and greater than about 680 nm.

In a preferred embodiment, photodetector 20 may include an image intensifier having a viewing lens or screen 22 mounted on the output thereof to allow for direct visual detection of fluorescence by the operator. In the alternative or in addition to the viewing eyepiece or screen, the output signal from the photodetector 20 may be relayed to a recording instrument, such as an oscilloscope or printer for presenting a graphical display of fluorescent spectra intensity. In yet another alternative, the photodetector may be in communication with a signal generator for generating and displaying a cleaning/disinfection signal when the fluorescent intensity at the measured 660–680 nm range has exceeded a predetermined threshold value. Signals may include for example, audible alarms, visible lights or LEDs, or any combination of the above.

An optional microprocessor based control unit 23 (shown in FIG. 3) having conventional interface hardware may be provided for receiving and interpreting the signals from the photodetector, and manipulating data as described above. The signal generator may be provided in communication with the microprocessor rather than photodetector 20. Microprocessor 23 may also be used for automated control of carcass testing, including automated scanning of carcasses, and/or directing carcasses positive for fecal or ingesta contamination to washing/disinfection stations.

Figure 3:
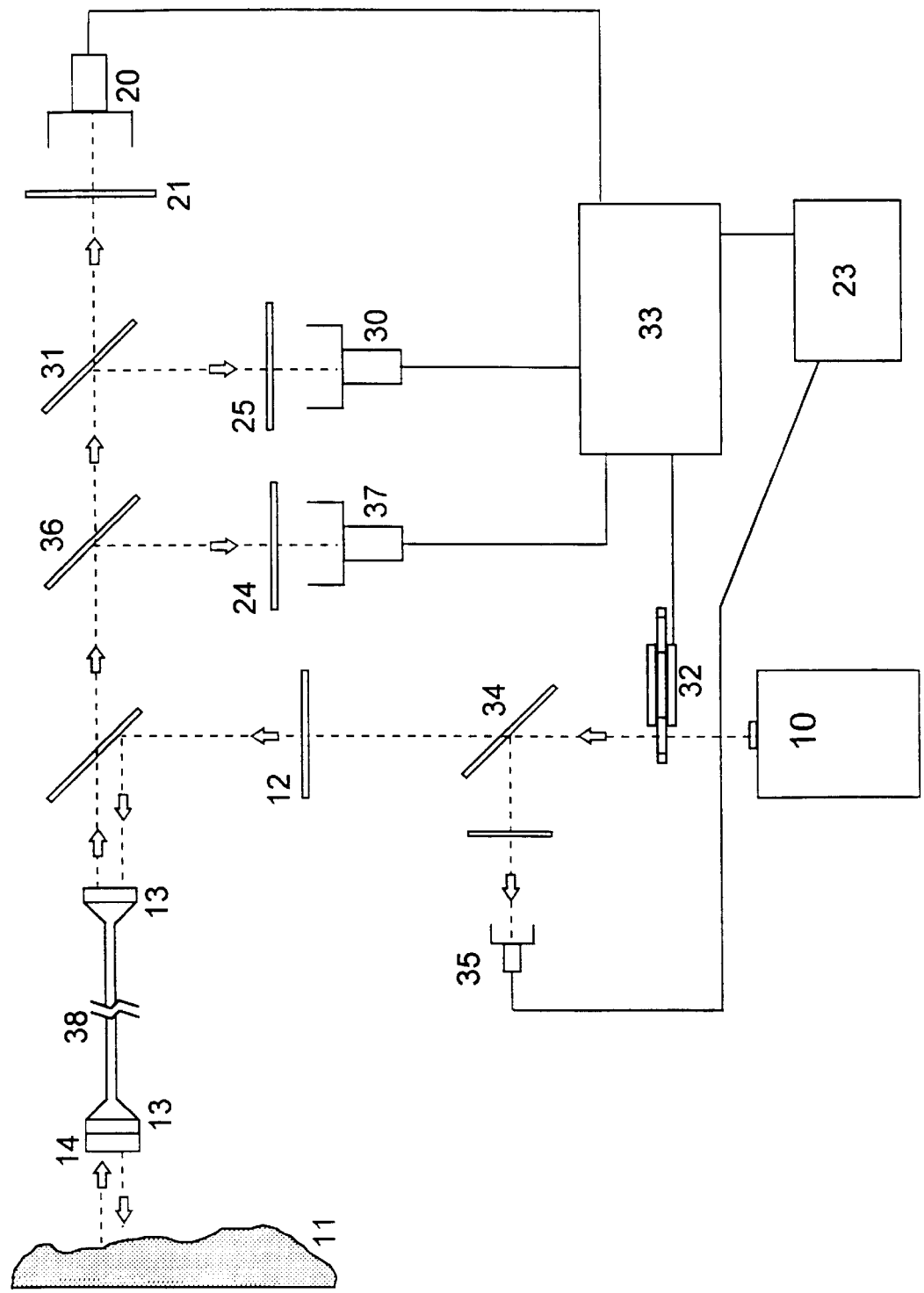
FIG. 3 shows an alternative embodiment of the apparatus.

A variety of optional modifications which may be made to the apparatus for use in the preferred embodiments are also shown in FIG. 3. For instance, photodetector 30 and cooperating dichroic mirror 31 may be provided for measurement intensity of baseline fluorescence (610–620 nm) for improving contrast as described hereinabove. Where quantitative measurements are to be made using phase sensitive technology, the apparatus may also include a frequency modulator such as chopper 32, lockin amplifier or gated integrator 33 in communication with chopper 32 and photodetectors 20 and 30, as well as beam splitter 34 and photodetector 35 for measuring the intensity of excitation light. Microprocessor 23 may then calculate the intensity of the emitted fluorescence at 660–680 nm from the phase shift and excitation light intensity data. Interference filters 25 and 21 centered at approximately 610 nm and 670 nm, respectively, can be placed before the photodetectors to reduce the stray light and increase the signal-to-noise ratio observed. Excitation light source 10 may also be equipped to provide an infrared beam which can be used as a reference for scattered light intensity from the carcass and as a distance probe from the carcass. In this event, an additional IR reflecting dichroic mirror 36 and IR photodetector 37 fitted with an IR interference filter 24 are included.

The apparatus may be constructed as a hand-held device for manual testing, or as a fixed pass-through box or station positioned along the slaughterhouse line for automated testing. Fiber optics 38 may be provided as shown in FIG. 3 for directing excitation light onto the carcass and/or collecting emitted fluorescent light. The fiber optic may be fitted with lenses 13 to collimate the laser beam to a given size on the carcass and to assist in the collection of emitted light. The fiber optic may also be fitted with a disposable tip 14 to gauge the distance between the excitation source and the carcass reproducibly and accurately. This is beneficial when quantifying contamination on the carcass.

The following examples are intended only to further illustrate the invention and are not intended to limit the scope of the invention which is defined by the claims.

EXAMPLE 1

Figure 4:
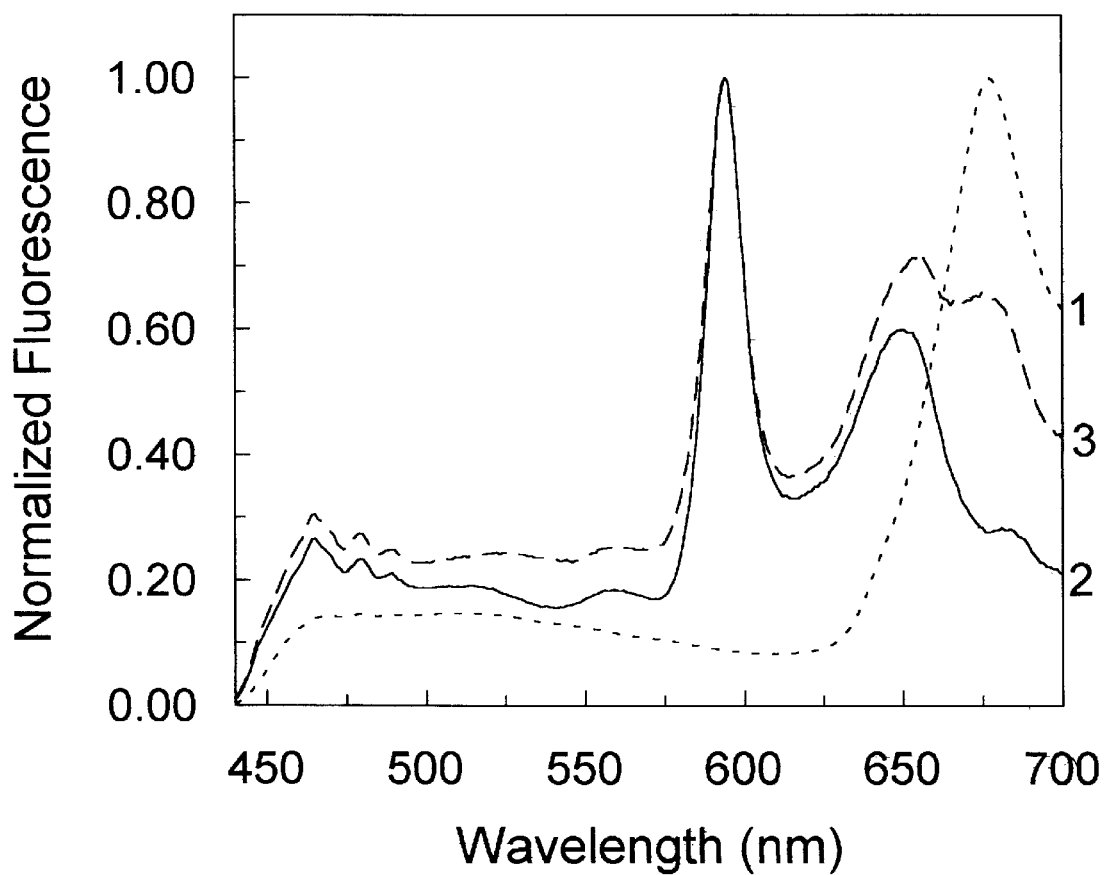
FIG. 4 is the emission spectrum of feces contaminated beef samples excited at 430 nm using a 455 cutoff filter to collect fluorescence and to block scattered light.
Figure 5:
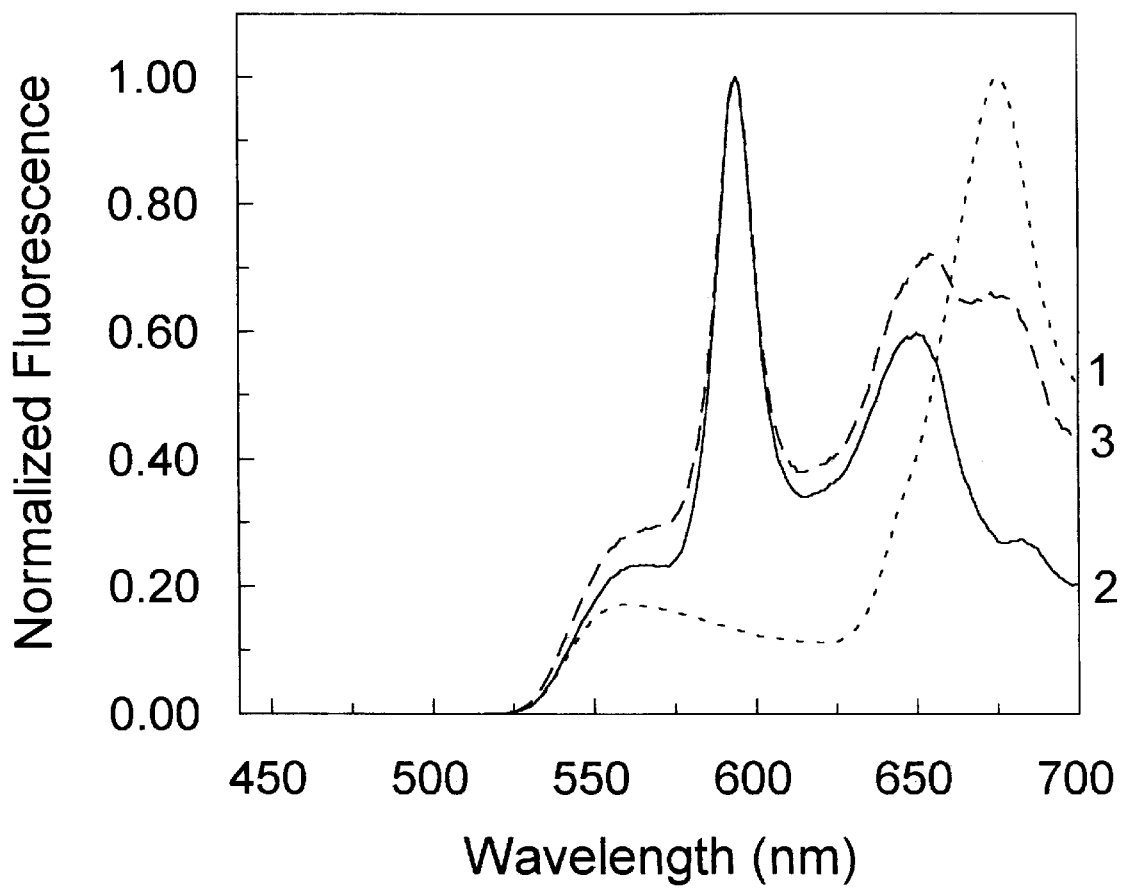
FIG. 5 is the emission spectrum of feces contaminated beef samples excited at 430 nm using a 555 cutoff filter to collect fluorescence and to block scattered light.

Solid cuts of fresh beef were intentionally contaminated with ingesta obtained from the rumen of a cow fed an alfalfa hay/corn diet, and placed into a 45° angled glass cuvette like that shown in FIG. 2. The amount of ingesta placed on the surface of the beef was too dilute to be seen with the naked eye. The contaminated beef samples were then illuminated with excitation light at 430 nm using a 4.25 nm bandpass on the excitation monochrometer. Fluorescent light emitted from the meat sample was detected with a 4.25 nm bandpass on the emission monochrometer. These experiments were performed with a SPEX FLUOROMAX fluorimeter (ISA Jobin Yvon-SPEX, Edison, N.J.). The results are shown in FIGS. 4 and 5. The emission spectra in FIGS. 4 and 5 are 1, contaminating ingesta only; 2, uncontaminated beef only; and 3, beef contaminated with ingesta. Contaminated samples showed a characteristic fluorescent emission at 670 to 675 nm.

EXAMPLE 2

A solid portion of fresh chicken (a drumstick) was intentionally contaminated at a small spot thereon with chicken feces and placed into a light-tight imaging chamber fitted with a CCD camera. The camera was linked to a computer that contained computer imaging software (CHEM IMAGER 4000, AlphaInnotech Corp., San Leandro, Calif.). The amount of ingesta placed onto the drumstick was too dilute to be seen with the naked eye using ambient light. The chamber was closed and the meat sample was then illuminated with an excitation light (actinic blue aquarium light, Energy Savers Unlimited Inc., Harbor City, Calif.) fitted with a 430 nm (10 nm bandpass) optical filter (CVI Laser Corp., Albuquerque, N. Mex.). The fluorescent light emitted from the chicken sample and associated contamination was observed and saved as a computer file using the CCD camera/computer/software package. The camera which was fitted with replaceable 610 nm (10 nm bandpass) and 670 nm (10 nm bandpass) optical filters was used to capture fluorescent images given off from the sample. The imaging software was also used to subtract the 610 nm image from the 670 nm image. Under these conditions, a photo was produced that showed a white spot contrasted against a black background with the white spot being located where the fecal contamination had been placed on the drumstick. The black background indicates that there was little interfering background light emanating from scattered light or from other fluorescing media. Photos of uncontaminated control samples showed only the dark background.

It is understood that the foregoing detailed description is given merely by way of illustration and that modifications and variations may be made therein without departing from the spirit and scope of the invention.

We claim:

1. A method for detecting ingesta or fecal contamination on a surface of an animal carcass during or after slaughter comprising:
   a. illuminating the surface of a carcass of an animal with UV or visible light having a wavelength effective to elicit fluorescence of feces of an animal consuming plants containing photosynthetic pigments at a wavelength between about 660 to 680 nm, and
   b. detecting fluorescent light emission from said surface at a wavelength between about 660 to 680 nm,
      wherein detection of fluorescent light emission at said wavelength between about 660 to 680 nm is an indication of the presence of ingesta or fecal material on said surface of said carcass, and further wherein said illuminating and said detecting are conducted during slaughter or within about 1 hour of completion of slaughter of said animal.

2. The method as described in claim 1 wherein said animal is selected from the group consisting of bovine, poultry, porcine, ovine, and caprine.

3. The method as described in claim 1 wherein said detecting comprises quantitatively measuring said fluorescent light emission at said wavelength between about 660 to 680 nm.

4. The method as described in claim 3 further comprising quantitatively measuring the intensity of fluorescent light emission from said surface at a wavelength between about 610 to 620 nm and subtracting or normalizing the intensity of the measured fluorescence at said wavelength between about 610–620 nm from the intensity of the measured fluorescence at said wavelength between about 660 to 680 nm.

5. The method as described in claim 1 wherein said detecting further comprises filtering out one or more wavelengths of fluorescent light emission from said surface greater than about 680 nm or lower than about 660 nm.

6. The method as described in claim 5 comprising filtering out wavelengths of fluorescent light emission from said surface between about 460–540 nm.

7. The method as described in claim 1 wherein the wavelength of said fluorescent light emission is between about 670–675 nm.

8. The method as described in claim 1 wherein said method further comprises washing or decontaminating any animal carcass wherein fluorescent light emission from said carcass at a wavelength between about 660 to 680 is detected.

9. The method as described in claim 8 further comprising repeating the steps of illuminating and detecting of said carcass after said washing or decontaminating until no fluorescent light emission having a wavelength between about 660 to 680 is detected.

10. The method as described in claim 1 wherein said illuminating comprises illuminating said surface with light having said wavelength between about 300 to 600 nm.

11. The method as described in claim 10 wherein said illuminating comprises illuminating said surface with light having said wavelength selected from the group consisting of between about 400 to 440 nm, between about 510 to 600 nm, and combinations thereof.

12. The method as described in claim 11 wherein said illuminating comprises illuminating said surface with light having said wavelength between about 400 to 440 nm.

13. The method as described in claim 12 wherein said illuminating comprises illuminating said surface with light having said wavelength between about 410 to 430 nm.

14. The method as described in claim 11 wherein said illuminating comprises illuminating said surface with light having a wavelength between about 510 to 600 nm.

15. The method as described in claim 14 wherein said illuminating comprises illuminating said surface with light having said wavelength between about 520 to 540 nm.

16. The method as described in claim 1 wherein said illuminating and said detecting are conducted at more than one location along a slaughterhouse line, and determining the location on said line wherein said carcass is contaminated with ingesta or fecal material.

17. A method as described in claim 1 wherein said photosynthetic pigments contained in said plants comprise chlorophyll.

18. A method for detecting ingesta or fecal contamination on a surface of an animal carcass during or after slaughter comprising:
   a. illuminating the surface of a carcass of an animal with UV or visible light having a wavelength effective to elicit fluorescence of feces of an animal consuming plants containing photosynthetic pigments at a wavelength between about 660 to 680 nm, and
   b. detecting fluorescent light emission from said surface at a wavelength between about 660 to 680 nm,
      wherein detection of fluorescent light emission at said wavelength between about 660 to 680 nm is an indication of the presence of ingesta or fecal material on said surface of said carcass, and further wherein said illuminating and said detecting are conducted at more than one location along a slaughterhouse line, and determining the location on said line wherein said carcass is contaminated with ingesta or fecal material.

19. A method for detecting ingesta or fecal contamination on a surface of an animal carcass during or after slaughter comprising:
   a. illuminating the surface of a carcass of an animal with UV or visible light having a wavelength effective to elicit fluorescence of feces of an animal consuming plants containing photosynthetic pigments at a wavelength between about 660 to 680 nm, and
   b. detecting fluorescent light emission from said surface at a wavelength between about 660 to 680 nm,
      wherein detection of fluorescent light emission at said wavelength between about 660 to 680 nm is an indication of the presence of ingesta or fecal material on said surface of said carcass, and further wherein said illuminating and said detecting are conducted within about 2 hours after the initiation of slaughter of said animal.

20. A method for detecting ingesta or fecal contamination on a surface of an animal carcass during or after slaughter comprising:
   a. illuminating the surface of a carcass of an animal with UV or visible light having a wavelength effective to elicit fluorescence of feces of an animal consuming plants containing photosynthetic pigments at a wavelength between about 660 to 680 nm,
   b. detecting fluorescent light emission from said surface at a wavelength between about 660 to 680 nm, wherein detection of fluorescent light emission at said wavelength between about 660 to 680 nm is an indication of the presence of ingesta or fecal material on said surface of said carcass, and
   c. washing or decontaminating any animal carcass wherein fluorescent light emission from said carcass at a wavelength between about 660 to 680 is detected.

* * * * *